United States Patent [19]

Giacalone

[11] Patent Number: 4,568,340
[45] Date of Patent: Feb. 4, 1986

[54] EXTERNAL CATHETER FOR INCONTINENT MALES

[76] Inventor: Joseph J. Giacalone, 2547 La Serena, Escondido, Calif. 92025

[21] Appl. No.: 559,344

[22] Filed: Dec. 8, 1983

[51] Int. Cl.$^4$ ............................................. A61F 5/44
[52] U.S. Cl. ........................................ 604/353; 2/405
[58] Field of Search ........... 2/405; 285/260, DIG. 16, 285/208; 604/346–353

[56] References Cited

U.S. PATENT DOCUMENTS 3,721,243 3/1973 Hesterman et al. ................. 604/353
3,999,550 12/1926 Martin ................................. 604/353

Primary Examiner—J. L. Kruter
Attorney, Agent, or Firm—Frank D. Gilliam

[57] ABSTRACT

An improved external catheter for incontinent males. The external catheter consists of three interrelated components. A generally tubular sheath having a fluid drainage tube connection at one end and a reinforcing ring at the other is adapted to fit loosely over the penis with the ring at the base of the penis. A frusto-conical seal of elastic material having a reinforcing ring at the base end is adapted to fit within the sheath with the ring at the base of the penis adjacent to the sheath ring. The wall of the frustom extends along the penis in snug engagement therewith. A nether garment to be worn by the patient has a penis-receiving hole surrounded by a collar. The collar has a circular channel means with the channel opening extending outwardly away from the penis. With all three components in place, the two rings are extended slightly and snapped into the collar channel, sealing the ring and sheath together and using the nether garment to resist forces tending to remove the sheath. This external catheter assembly is extremely resistant to seepage of urine or to being forced off of the penis by a sudden large flow of urine.

6 Claims, 5 Drawing Figures

EXTERNAL CATHETER FOR INCONTINENT MALES

BACKGROUND OF THE INVENTION

This invention relates in general to urine drainage systems for incontinent males and, more specifically, to an improved external catheter system having improved resistance to leakage.

With advanced age, disease, nerve damage or the like, people sometimes lose the ability to control the flow of urine. There may be a gradual leakage of urine with an occasional sudden heavy flow of urine.

Attempts have been made to drain the urine both with internal catheters extending into the urethra and with external catheters which (for males) includes a sheath surrounding the penis and connected to a drain line to convey urine to a receptacle.

Internal catheters function well for short periods, but are too likely to cause infections or other problems in the bladder or urinary tract to permit long-term use.

External catheters have been found to be useful where a slow, steady urine flow occurs. But many problems occur where the urine flow is irregular, which is the usual case. If the sheath is not tight, seepage is likely to occur with resulting embarrassing odors and clothing stains. A very tight sheath may cause pain during involuntary erections. Where there is a sudden large flow or "burst" of urine, the entire sheath may be forced off of the penis causing a spillage of a large quantity of urine.

The straps used with some devices to hold the sheath in a place are uncomfortable and likely to fail. Also, a sudden large urine flow exceeding the short-term capacity of the drain line is likely to back up, expand the sheath and leak out the top.

Thus, there is a continuing need for improved external catheters for males which overcome these problems.

SUMMARY OF THE INVENTION

An external catheter assembly for incontinent males having an improved sealing arrangement resistant to leakage. The assembly consists of three parts. An elastic, generally frusto-conical, sealing means is provided having a first reinforcing ring at the base. The seal fits over the penis with the seal ring at the base of the penis and the portion lying along the penis in elastic engagement therewith. A rubbery sheath (which may be loose or a close fit, as desired) fits over the length of the penis with a connection to a drain tube at the end of the penis and a sheath reinforcing ring at the base of the penis adjacent to the seal ring. A nether garment, preferably similar to conventional briefs, surrounds the lower torso with a frontal opening through which the penis is extended. A collar surrounds the opening and is secured to the briefs. The collar includes a circular channel means with the channel opening oriented away from the penis. The sheath and seal reinforcing rings are sufficiently elastic to permit them to be stretched slightly and snapped into the collar channel, sealing them together.

As detailed below, forces from a sudden surge of urine do not cause leakage and cannot force the sheath off of the penis because of the orientation of the sealing means and the attachment to the nether garment.

BRIEF DESCRIPTION OF THE DRAWING

Details of the invention, and of a preferred embodiment thereof, will be further understood upon reference to the drawing, wherein.

DETAILED DESCRIPTION OF THE INVENTION

Figure 1:
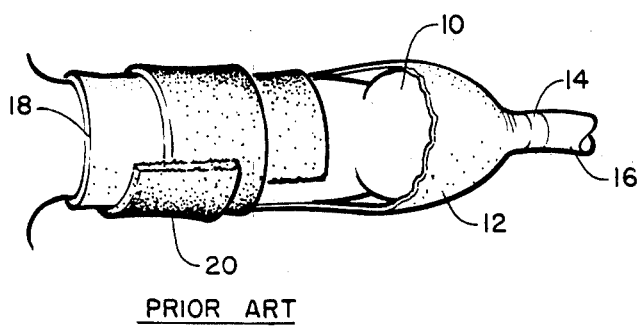
FIG. 1 is a schematic side view of an external catheter according to the prior art.

Referring now to FIG. 1, there is seen a penis 10 with a conventional external catheter means in place. The prior art external catheter assembly consists of a rubbery, condom-like, sheath 12 having a connection 14 to a drainage tube 16 at one end. The sheath may have a reinforcing ring 18 at the other end. When purchased, sheath 12 may be rolled up and may be unrolled onto the penis. A piece of adhesive tape 20 is wrapped fairly tightly around sheath 12 to help hold the sheath in place and help restrict leakage back up sheath 12 and out past ring 18.

The external catheter of FIG. 1, and several variations thereof, have been in use for some time, but present several problems. To limit leakage, sheath 12 and tape 20 must be rather tight and tend to irritate the skin of the penis. Also, pressure against tape 20 during an involuntary erection can be painful. A sudden release of urine, when the penis is quite flaccid, can cause leakage of urine between sheath and penis and, in some cases, cause the entire sheath to be forced off of the penis. The resulting odors and stains are very embarrassing to the user.

Attempts have been made to improve leakage resistance and prevent sheath loss by adding double-stick tape between penis 10 and sheath 12, by overlapping the reinforcing ring 18 edge and the adjacent skin with tape or by painting a silicone adhesive onto penis 10 before unrolling sheath 12. While these variations help overcome the leakage problem somewhat, the adhesive causes irritation to the skin of the penis and applying and removing the adhesive coating or tape can be difficult and painful.

Figure 2:
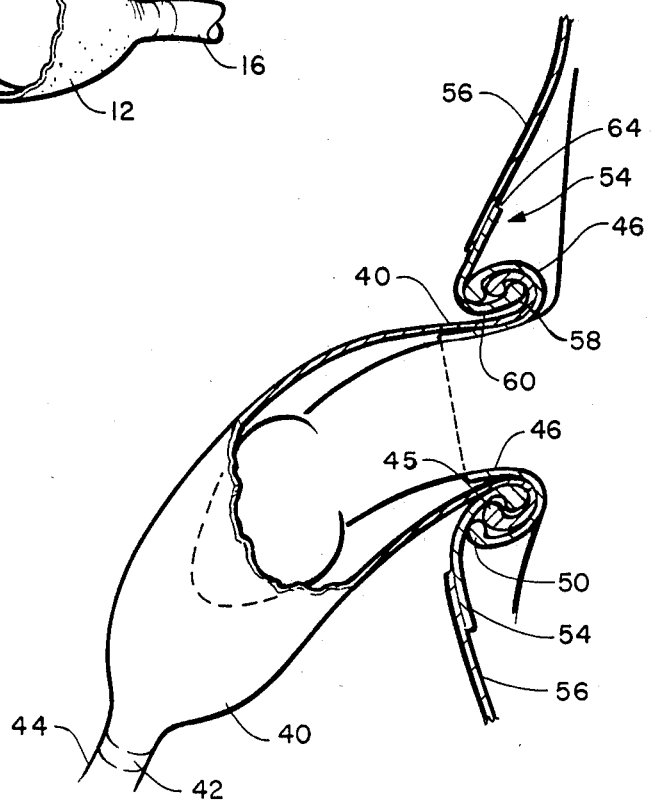
FIG. 2 is a schematic side view, partially cut-away, of the external catheter of this invention.

The improved external catheter of this invention is schematically shown in elevation in FIG. 2, with the assembly partially cut-away along the portion near the base of the penis for clarity. Here sheath 40 has a connection 42 to a drain line 44 at one end and a reinforcing ring 45 at the other. Sheath 40, connection 42 and drain line 44 may be molded in one piece, if desired. Drain line 44 leads to any suitable collection bag or the like. Sheath 40 is generally similar to the prior art sheath 12, except that here the sheath need not be irritatingly tight to prevent leakage. Sheath 40 may be manufactured from any suitable rubbery or plastic urine-impervious material.

Figure 3:
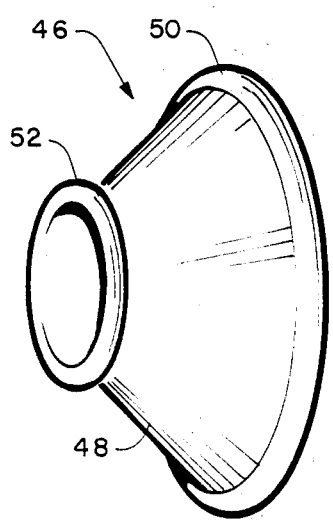
FIG. 3 is a perspective view of the seal means.

As seen in FIGS. 2 and 3, an internal seal means 46 is located within sheath 40. Seal means 46 includes a generally frusto-conical elastic wall or membrane 48 with a first, or seal, reinforcing ring 50 at the base and a second reinforcing ring 52 at the outer edge of the wall of the seal means. While ring 52 is preferred in some cases, it may be eliminated where wall 48 has sufficient inherent edge strength.

Figure 4:
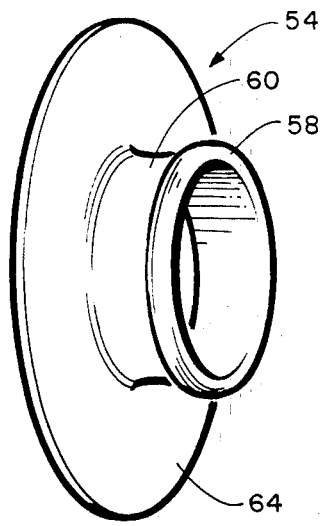
FIG. 4 is a perspective view of the collar means.

As seen in FIGS. 2 and 4, a ring-like collar 54 is secured in an opening in a nether garment 56. The penis 10 extends through collar 54 next to sheath reinforcing ring 45 and seal reinforcing ring 50. Collar 54 has a generally channel-like cross section, facing outward, with an inner lip 58 and a channel base 60. Rings 45 and 50 may be stretched slightly and snapped over lip 58 to be retained thereby against channel base 60. Either of the rings 45 and 50 can be nearest lip 58 when snapped into the channel.

Collar 54 may be formed from any suitable material. Polyproplyene is preferred since it has a smooth, easily cleaned surface and is easily molded into the desired shape.

Figure 5:
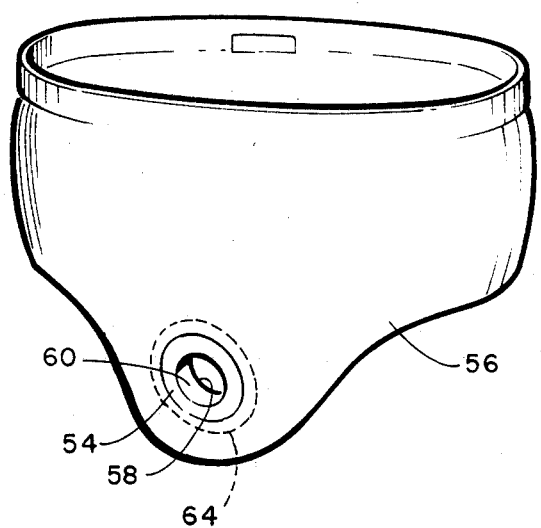
FIG. 5 is a perspective view of briefs with the collar means of FIG. 4 in place.

As seen in FIG. 5, collar 54 may be fastened into a hole in any suitable nether garment 56 by any conventional method, such as by sonic welding of flange 64 to the fabric or sewing through the fabric and flange. Typically garment 56 may be conventional men's briefs.

The catheter system may be made in several different diameters to accommodate penises of different diameters. In most cases, collar 54 may have an inside diameter of about 1.45 inches. The diameter of lip 58 then might be about 1.7 inches, to allow sheath and seal rings 45 and 50 having diameters of about 1.5 inches to be snapped thereover and to be held in place.

With the prior art arrangement of FIG. 1, a sudden heavy flow of urine beyond the immediate capacity of the drain tube will tend to force sheath 12 (and any tape 20) away from the penis, allowing leakage between skin and sheath out the open end of sheath 12 and may force sheath 12 entirely off of the penis 10. With the novel catheter assembly as seen in FIG. 2, a sudden flow of urine will tend to expand sheath 40 (which can be a loose fit and of easily expandable material if desired), the pressure will tend to press the inner seal 46 wall and apex ring 52 more tightly against the penis, preventing leakage. Even with a very great and sudden urine flow, sheath 40 will be held in place by collar 54 and garment 56.

While certain preferred dimensions, materials and arrangements were described in conjunction with the above description of a preferred embodiment, these may be varied, where suitable, with similar results. For example, sheath 40 may be formed from any suitable material and may be snug or loose, as desired.

Other modifications, variations and ramifications of this invention will occur to those skilled in the art upon reading this disclosure. Those are intended to be included within the scope of this invention, as defined in the appended claims.

I claim:

1. An external catheter system for incontinent males which comprises, an inner seal means comprising an elastic, generally frustro-conical wall membrane having reinforcing seal rings at each end, adapted to being positioned on a penis with the greater diameter seal ring positioned at the base of the penis and spaced therefrom and a portion of the wall membrane of the seal means extending along the penis adjacent said base in elastic contact therewith, said inner seal means disposed within a generally tubular sheath means, said generally tubular sheath means having a reinforcing sheath ring at one end and a connection means adapted to be connected to a drainage tube at the other end, said sheath being adapted to enclose a penis with said sheath ring adjacent to said greater diameter seal ring and said connection means adjacent to the end of the penis, and nether garment means to engage and surround the lower trunk of a wearer, said garment having an opening in which a collar having an axially extending central opening is secured, said collar having a flange portion which is fastened to the nether garment and a channel base portion extending toward the wearer's body terminating in an inner lip portion, said sheath means and said inner seal means extend longitudinally through the central openings, said reinforcing seal ring and said reinforcing sheath ring are positioned over the inner lip portion of the collar, within the said inner seal means to provide an effective removable type urine seal.

2. The external catheter system according to claim 1 wherein said nether garment is substantially similar to conventional men's briefs, with said collar installed in place of the usual fly opening.

3. The external catheter system according to claim 1 wherein said collar is formed from polypropylene and is secured to the edge of the hole in said nether garment by sonic welding.

4. The external catheter system according to claim 1 wherein said sheath, connection and drain tube are manufactured as a single integral unit.

5. The external catheter system according to claim 1 wherein the material of construction and the diameter of said sheath are selected to provide engagement with said penis.

6. The external catheter system according to claim 1 wherein the diameter of said sheath is selected to provide loose fit on said penis.

* * * * *